(12) United States Patent
Barela et al.

(10) Patent No.: US 10,539,707 B2
(45) Date of Patent: Jan. 21, 2020

(54) SYNCHRONIZED MARKERS FOR X-RAY SYSTEMS

(71) Applicant: The Government of the United States of America, as represented by the Secretary of Homeland Security, Washington, DC (US)

(72) Inventors: Cecilia Barela, Washington, DC (US); Tye McGrath, Washington, DC (US)

(73) Assignee: The Government of the United States of America, as represented by the Secretary of Homeland Security, Washington, DC (US)

( * ) Notice: Subject to any disclaimer, the term of this patent is extended or adjusted under 35 U.S.C. 154(b) by 119 days.

(21) Appl. No.: 15/941,657

(22) Filed: Mar. 30, 2018

(65) Prior Publication Data

US 2018/0284314 A1    Oct. 4, 2018

Related U.S. Application Data

(60) Provisional application No. 62/478,644, filed on Mar. 30, 2017.

(51) Int. Cl.
*G01V 5/00*     (2006.01)
*B65G 49/00*    (2006.01)
*G01N 23/04*    (2018.01)

(52) U.S. Cl.
CPC ......... *G01V 5/0016* (2013.01); *B65G 49/00* (2013.01); *G01N 23/04* (2013.01); *B65G 2201/0264* (2013.01); *G01N 2223/303* (2013.01); *G01N 2223/417* (2013.01)

(58) Field of Classification Search
CPC ............ G06K 2209/01; G06K 9/2054; G01V 5/0008; G01V 5/0016; G09F 3/0294; G01T 7/08
See application file for complete search history.

(56) References Cited

U.S. PATENT DOCUMENTS

| | | | |
|---|---|---|---|
| 6,967,579 B1 | 11/2005 | Elizondo | |
| 7,286,634 B2 | 10/2007 | Sommer, Jr. et al. | |
| 7,876,884 B2 * | 1/2011 | Davis | G01N 23/04 |
| | | | 378/162 |
| 8,014,493 B2 | 9/2011 | Roux et al. | |
| 8,401,146 B2 | 3/2013 | Vorhees | |
| 8,861,676 B2 | 10/2014 | Bloesl et al. | |

(Continued)

*Primary Examiner* — Yara B Green
(74) *Attorney, Agent, or Firm* — Lavanya Ratnam; William Washington; Kelly G. Hyndman

(57) ABSTRACT

Various embodiments of the present invention are directed towards a system and method for synchronized markers. A multiple-scanner X-ray system includes a belt passing by an upper X-ray scanner and a lower X-ray scanner. An upper belt portion is conveyed in a first direction by the upper X-ray scanner and a lower belt portion is conveyed in a second direction opposite the first direction by the lower X-ray scanner, to obtain upper and lower X-rays. A plurality of X-ray reactive markers are positionally synchronized relative to each other and the belt and conveyed by the belt to cause upper visual marker information, corresponding to a visual appearance of the upper scanned belt section, to be consistent with i) upper X-ray marker information of the upper X-ray, and ii) lower X-ray marker information of the lower X-ray.

20 Claims, 10 Drawing Sheets

(56) References Cited

U.S. PATENT DOCUMENTS 8,983,027 B2 * 3/2015 Kuesel .................. B65G 43/02
378/209
9,470,816 B2 * 10/2016 Eshetu ..................... G09F 3/02

* cited by examiner

SYNCHRONIZED MARKERS FOR X-RAY SYSTEMS

CROSS-REFERENCE TO RELATED APPLICATIONS

This application claims the benefit of U.S. Provisional Application No. 62/478,644 entitled "X-ray Belt Photo Opaque Marker and Point of Reference," filed on Mar. 30, 2017, which is incorporated herein by reference in its entirety.

STATEMENT OF GOVERNMENT INTEREST

The present invention was made by one or more employees of the United States Department of Homeland Security in the performance of official duties, and, thus the claimed invention may be manufactured, used, licensed by or for the United States without the payment of any royalties thereon.

FIELD OF THE INVENTION

The present invention relates generally to the field of X-ray systems, and more specifically to synchronized markers used at security checkpoints to positively identify scanned items.

BACKGROUND OF THE INVENTION

Security Officers pulling misidentified items for inspection has been an issue since X-ray machines were incorporated into the security environment. Every time this occurs at an airport, the airport needs to report it as an X-ray Access Control Event. The use of a Manual Diverter Roller (MDR) and Alternate Viewing Station (AVS) in the checkpoint scanning process increases the instances of wrong bag pulls. The X-ray Security Officer viewing the X-ray display can select an item for additional screening. However, due to the nature of some X-ray systems, the x-ray Security officer may need to advance the belt forward to enable the item in question to exit the machine and be pulled from the system's tube to the MDR. The item sits on the MDR, sometimes behind other items, awaiting inspection. When the Property Search Officer (PSO) takes the suspect item from the MDR to the AVS and pulls up the X-ray image, the PSO may then realize that the contents of the bag and the X-ray image do not match. This may be due to the X-ray Security Officer having selected the wrong (i.e., mismatched) bag for secondary search. It can be difficult to locate the actual item that the X-ray officer wanted to select for additional screening, and the passenger may not still be located in the security checkpoint screening area and may have boarded a plane. Furthermore, the item may be so dangerous that an airport will have to force everyone out of the sterile area, sweep the airport, and rescreen all passengers. This can create logistical nightmares for airport operations with the potential to become catastrophic events, due to such X-ray access control violations. A wrong bag pull represents a temporary loss of security containment that can be minor or escalate into a highly publicized media event or worse, a true risk to the transportation security network.

Airports and vendors have tried other methods to prevent this type of access control event: confer and concur where two officers make a decision on whether the correct bag/item is being pulled, using reflective numbers on bins, arranging orientations of like items in different configurations, and so on. These solutions do not work because they do not address the root cause or they require TSO assistance or the passenger to divest differently. In some instances, markers used on belts create confusion in single-scanner X-ray systems (markers appearing backward when the upper and lower belt sections are imaged together in a bottom-up scanner), and would be completely unworkable in multiple-scanner situation (where double or repeat markers would appear in the composite images, resulting in inability to tell which marker happened to be located on a top surface of the belt).

SUMMARY OF THE INVENTION

Embodiments described herein relate to photo opaque or reflective (X-ray reactive) markers being used with a belt on X-ray systems including a plurality of X-ray sources, to provide synchronized points of reference for security officers as displayed on the X-ray monitor displays and as evident visually on the X-ray belt, enabling accurate tracking and selection of items for additional inspection. More particularly, the invention relates to the process of placing, as well as the use of a belt which contains, synchronized markers on the X-ray belt to provide consistent points of reference in a plurality of X-rays regardless of a position of the belt. The application of this method and process can be used on various types of X-ray machines with a variety of markers. The careful spatial synchronization and placement of makers enables the consistent marker capability, particularly on multiple-scanner X-ray machines having offsets between the plurality of scanners.

Furthermore, additional challenges overcome by the presently described systems involve overcoming arbitrary offsets between either of the X-ray images and the visual appearance of the belt. For example, even within a given X-ray image showing various items, one or more of the item(s) displayed could have already physically moved out of the imaging section of the X-ray machine, such that the displayed item(s) no longer correspond to the physical appearance of the belt items.

Described herein are systems and methods for positioning markers on X-ray systems, such as those located at airport security checkpoints, to provide consistent and spatially synchronized points of reference on the X-ray display and physical appearance on the X-ray belt, for security officers to track and select items for additional inspection.

Other features and aspects of the invention will become apparent from the following detailed description, which taken in conjunction with the accompanying drawings illustrate, by way of example, the features in accordance with embodiments of the invention. This summary is not intended to identify key or essential features of the claimed subject matter, nor is it intended to limit the scope of the invention, which is defined solely by the claims attached hereto.

BRIEF DESCRIPTION OF THE DRAWINGS

One or more example embodiments of the present invention are described in detail with reference to the following drawings.

These drawings are not intended to be exhaustive or to limit the invention to the precise form(s) disclosed. It should be understood that the present invention can be practiced with modification and alteration, and that the invention is limited only by the claims and the equivalents thereof.

DETAILED DESCRIPTION OF THE INVENTION

An example embodiment can include a reflective/photo opaque X-ray reactive marker, adhesive for adhering the markers to the X-ray belt, and a process to place the markers to provide consistent points of reference on the X-ray monitor and X-ray belt, regardless of the position of the belt. In other embodiments, the belt can incorporate markers on or within the belt, such that the belt, and/or systems incorporating such belts, are pre-equipped with the markers without a need to add the markers to the belt. Reflective/photo opaque markers, shapes, types, and sizes are interchangeable, and the process for placing the markers is configured for a given type of X-ray system and the corresponding setup procedure. In an embodiment, visual markers are placed on a lower edge outer surface of the X-ray belt, and the X-ray reactive markers are adhered to an inner surface of the X-ray belt (the inner surface being protected/shielded from items that are placed for scanning on the outer surface of the belt). The markers are set so that there is a visual marker evident on the belt regardless of belt position, and the marker is spaced to accommodate items such that a reference point can be located in front or behind the item. When an X-ray Security Officer decides to confirm an auto alarm or annotate an item, the Officer can refer to the marker seen on the X-ray screen, to use that reference marker as visually appearing on the belt when selecting the item for secondary screening. Accordingly, this system prevents incorrect bag pulls from occurring, and prevents temporary loss of security containment that could be minor or escalate into a highly-publicized media event or serve as a true risk to the transportation security network. Furthermore, the synchronized positioning of the markers enables unambiguous marking when used in multiple-scanner X-ray systems, without duplicating X-ray reactive markers, or causing visually confusing marker information to be displayed (e.g., reversed/backward X-ray images, ambiguity whether a marker seen in a composite X-ray is located on a lower or upper constituent X-ray, and so on).

Figure 1:
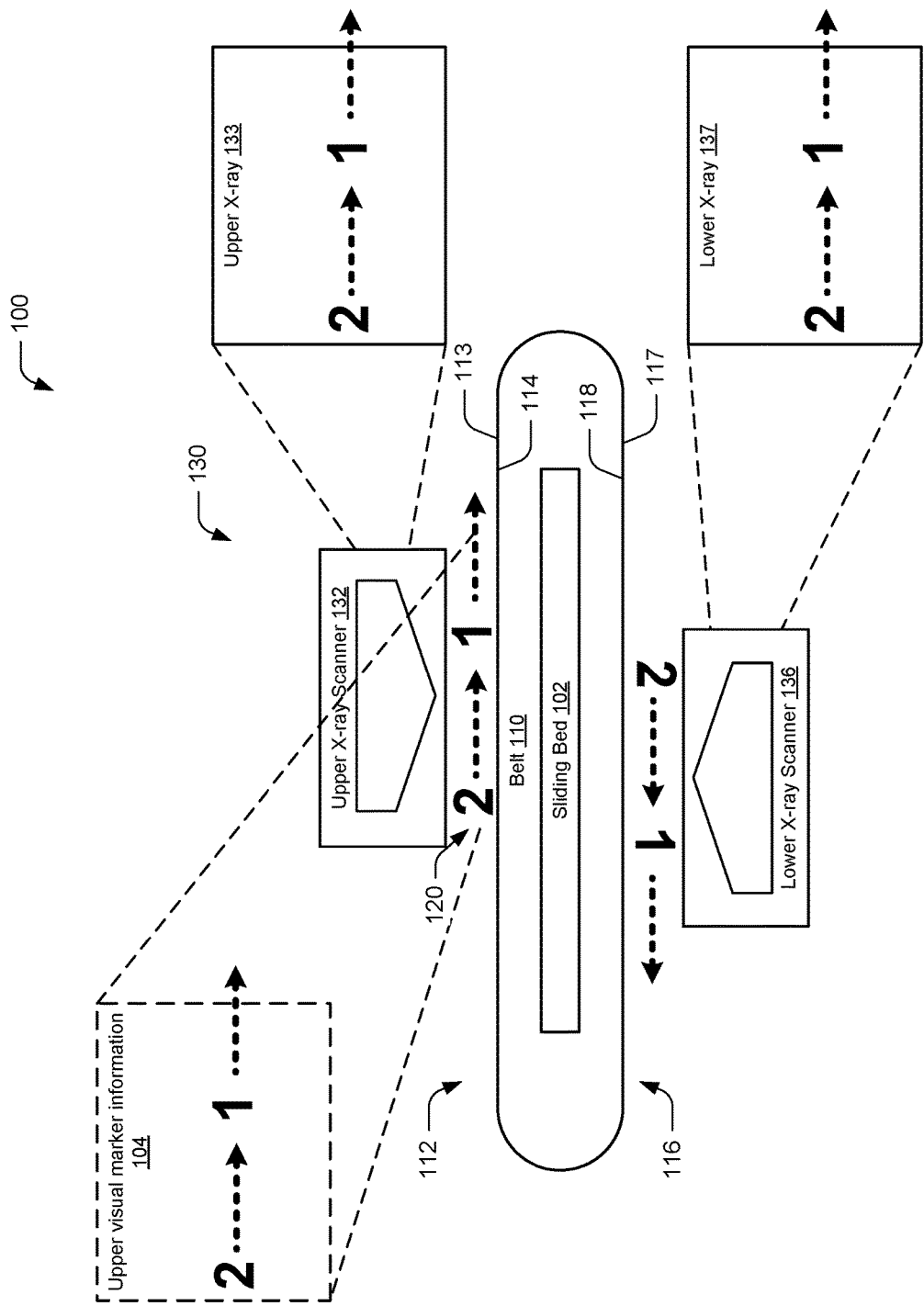
FIG. 1 illustrates an example system including synchronized markers apparent in an upper X-ray and a lower X-ray.

FIG. 1 illustrates an example system 100 including synchronized markers 120 apparent in an upper X-ray 133 and a lower X-ray 137. The markers 120 can include visual markers (see FIG. 2), which do not substantially reflect or absorb X-rays in a manner that would allow them to significantly appear on an X-ray image. For example, visual markers can be made of paper, plastic, cardboard, or other materials, and can be marked with ink, paint, or other pigments. Such visual markers can be made to visually contrast with the belt on which the visual markers will be used. In an embodiment, a visual marker can be formed as a black symbol including a white rectangular background, that when placed on a black belt, provides a visually distinctive visual marker.

The system 100 includes a plurality of X-ray sources and/or scanners. Some of the plurality of X-ray sources/scanners (e.g., side scanners/sources to obtain side-view X-ray images) are not illustrated in the drawings for the sake of simplicity. In the illustrated embodiment, two X-ray sources are shown. Furthermore, the terms X-ray source and/or X-ray scanner are used herein, which can refer to a source of X-rays, and/or a receiver of X-rays, operable to obtain a corresponding X-ray image such as upper X-ray 133 and lower X-ray 137. The upper X-ray scanner 132 images an upper belt portion 112 (through the belt 110 to the sliding bed 102), and the lower X-ray scanner 136 images a lower belt portion 116 (through the belt 110 to the sliding bed 102). For clarity, FIG. 1 illustrates operation of the multiple-scanner X-ray system resulting in multiple X-rays 133, 137, which can be displayed as a single composite X-ray for convenience (as shown in FIGS. 2 and 5A-5F). The multiple-scanner approach creates multiple challenges for synchronizing markers, challenges which are not present in single scanning X-ray systems.

The markers 120 also include X-ray reactive markers as Depicted in FIG. 1, made of materials that will produce a visual result on X-ray images 133, 137 of such markers. The X-ray reactive markers can be reactive via absorption of and/or opaqueness to X-ray beams, as well as via reflection of X-ray beams. Example materials include metal or other dense materials having desirable X-ray opaqueness/reflectance to appear in the resulting X-ray images. In an embodiment, the X-ray reactive markers are formed of a material that produces a subtle appearance in default X-ray images so as not to distract an operator, but that produces a more striking/contrasting appearance in adjusted X-ray images (such as by setting the X-ray system to scan for biological materials).

The markers are placed to be visually distinctive from items to be scanned. In an embodiment, the markers are placed toward an edge of the belt, for convenient viewing by an operator standing on that side of the belt and/or for convenient appearance of X-ray reactive markers at a lower edge of the corresponding X-ray images. For example, a marker can be placed approximately 1⅛ inches from a near edge of the belt.

As revealed by the appearance of the upper X-ray 133 and the lower X-ray 137, the X-ray reactive markers will appear in X-rays when they revolve into position at a scanning area of either upper or lower X-ray scanners 132 or 136. Thus, an X-ray reactive marker will show up whether it is traveling on the upper belt portion 112 or on the lower belt portion 116. This can have the potential to create confusion if the reference markers are not carefully spatially synchronized, e.g., through the use of pattern(s) of X-ray reactive markers as shown in FIG. 1, interspersed with pattern(s) of visual markers (see FIG. 2) and/or sub-patterns of additional markers.

Notably, the challenge to synchronize can arise when the length of the belt and the spacing between markers (e.g., to accommodate typical carry-on items) results in preventing the use of markers that are only X-ray reactive. For example, using straightforward numerical numbering around the belt circumference (e.g., numbers 1-10) can result in the lower X-ray showing numbers 6-10 while the upper X-ray shows numbers 1-5, creating ambiguity between numbers and which number is on an upper portion (e.g., the operator won't know whether to grab bag #2 or bag #7). Furthermore, the spacings and lengths can result in irregular patterns, e.g., sometimes marker 1 coincides with marker 6 on the composite X-ray, or sometimes marker 1 coincides with marker 5, depending on the belt rotation. Accordingly, in view of such difficulties, the present embodiments can adopt various patterns and sub-patterns, and use visual markers as well as X-ray reactive markers, to ensure consistency between the visual appearance of the upper belt, the upper X-ray, and the lower X-ray. Such approaches are successful, even when upper and lower markers mismatch (e.g., see FIG. 2 where the lower marker 0 aligns with the upper marker 3).

Figure 2:
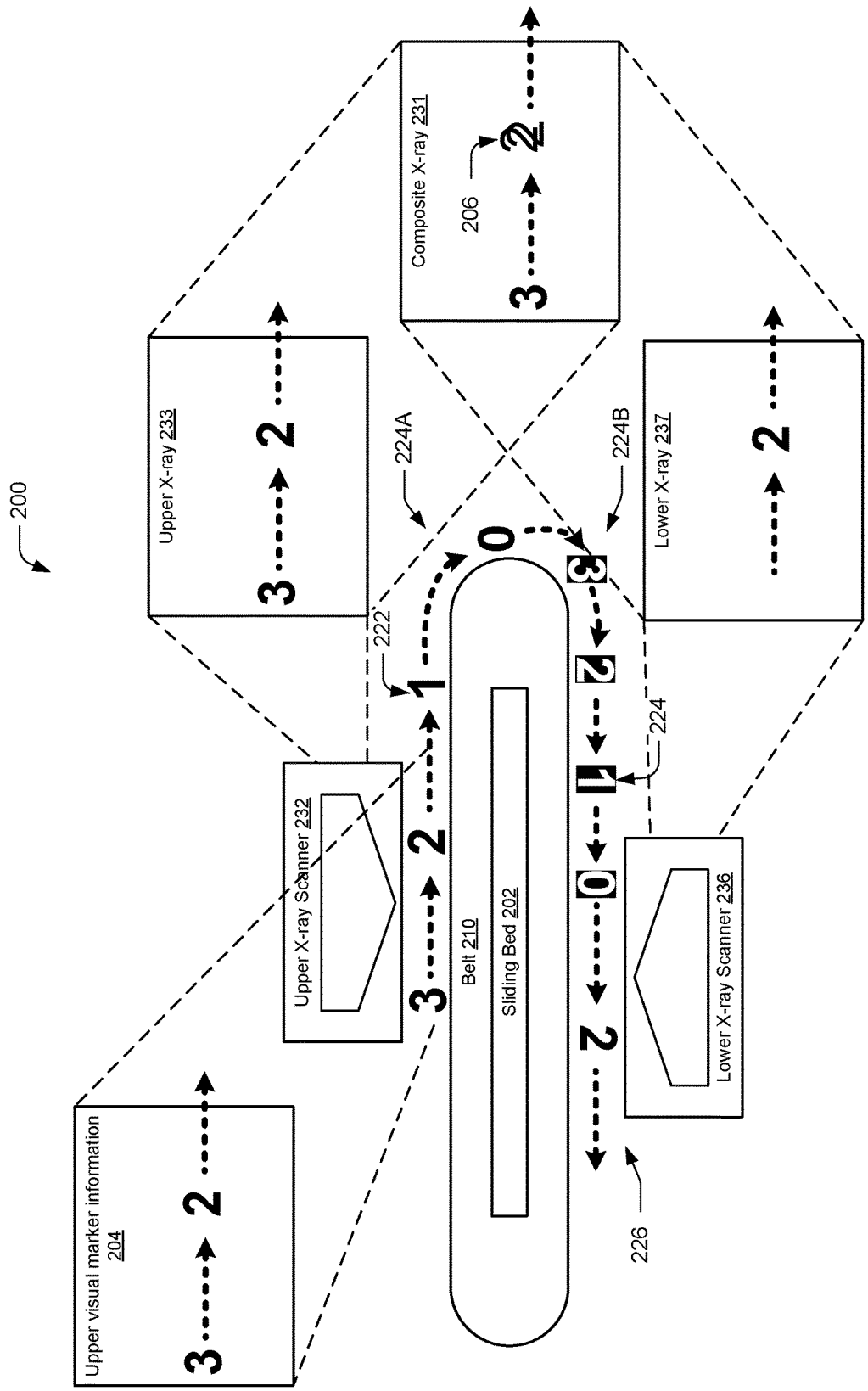
FIG. 2 illustrates an example system including synchronized markers apparent in a composite X-ray.

FIG. 2 illustrates an example system including synchronized markers 222, 224 apparent in a composite X-ray 231. The markers include X-ray reactive markers 222 and visual (e.g., not X-ray-reactive) markers arranged on the belt. As illustrated the upper visual marker information 204 matches the composite X-ray 231, and is not inconsistent with the upper or lower X-rays 233, 237. For example, although the marker "3" is missing from the lower X-ray 237, this missing information is restored in the composite X-ray 231.

Figure 5A:
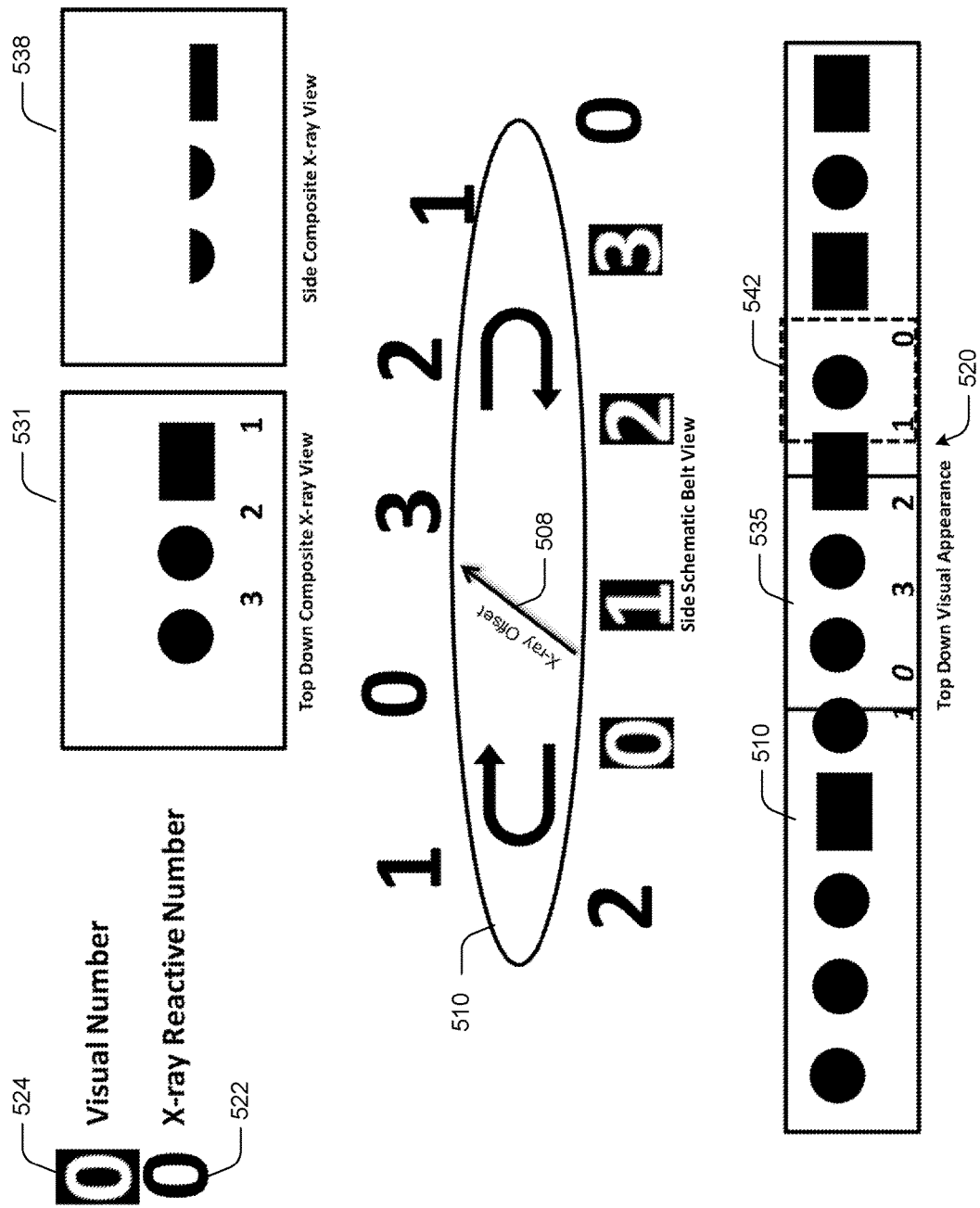
FIGS. 5A-5F illustrate an operation of an example system including synchronized markers apparent in a composite X-ray.

The markers as illustrated include a first pattern 224A of X-ray reactive markers, a second pattern 224B of visual markers, and a sub-pattern 226 of X-ray reactive markers. Although the markers are all visually depicted on an outer surface of the belt, X-ray reactive markers can be placed within the belt and/or on an inner surface of the belt. Furthermore, a given location on the belt can be provided with a combination of an X-ray reactive marker and a visual marker. For example, the X-ray reactive markers 222 can be placed on an inner surface of the belt, with corresponding visual markers (not shown) located on the corresponding outer surface of the belt, such that the visual marker information appearance of the marker location is consistent with an X-ray marker information appearance of the marker location. Furthermore, although not visible in the side-view of the belt, the markers can be placed in various locations along a width of the belt. For example, markers can be consistently placed near on edge of the belt (whether on the upper or lower surfaces). See, e.g., FIG. 5A depicting the top down visual appearance of the belt, where reference markers 520 are shown located toward the near edge of the belt.

As shown in the composite X-ray 231, the synchronized reference markers, whether X-ray reactive or visual, will create a consistent visual appearance whether viewed in person on an upper surface of the belt, or whether viewed on the composite X-ray monitor. This consistency can be based on the appearance of an X-ray reactive marker on a lower belt portion even if no X-ray reactive marker is on an upper belt portion (e.g., in a belt position where a visual marker is located on the upper belt portion, but its corresponding matching marker is located on the lower belt portion and composited in the composite X-ray image to overlap the visual marker area of the belt where no X-ray number is contained in the upper X-ray image).

As illustrated in FIG. 2, the upper X-ray scanner 232 images the X-ray reactive markers 3 and 2, depicted in the upper X-ray 233. The lower X-ray scanner 236 images the X-ray reactive marker 2, but not the visual marker 0. Because the visual marker 0 is located on an underside of the belt, the visual marker 0 is not visible to the operator looking at the visual appearance of the upper portion of the belt. The imaged marker 2 appears in the lower X-ray 237. Accordingly, even though there is a seeming mismatch between the visual marker 0 on the belt underside, and the X-ray reactive marker 3 on the belt upper side, the composite X-ray 231 remains a consistent match with the upper visual marker information 204 as viewed on the upper portion of the belt.

The composite X-ray 231 also demonstrates an insignificant misalignment between upper and lower X-ray reactive markers "2" (exaggerated for easier understanding). Such minor misalignments are well within the tolerance of acceptance for the illustrated numerical example markers, because a viewer can readily understand that the slightly misaligned symbol is a "2." Other types of symbols can be used with a similar variance in tolerance between minor misalignments. However, even a major misalignment, such as non-overlapping "2 2" that are seen within proximity to each other, are still readily discernible because the system can use all single-digit markers, such that it would be apparent to an operator that any double-digit symbols are due to misalignments or belt stretch over time, while still preserving unambiguously consistent markings.

Depending on the X-ray technology being set-up with reflective markers, the number of photo opaque/reflective markers and the number of non-reflective numbers varies. This is due to different lengths of belt, how the x-ray beam is triggered, auto calibration functions, and so on. In an embodiment, the markers are set so that there is a marker visible on the belt regardless of belt position, and the marker is spaced so that items will have a reference point in front or behind the item. When an X-ray Security Officer decides to confirm an auto alarm or annotate an item, they can refer to the marker depicted on the X-ray display, to use that reference marker when identifying the corresponding physically visible markers on the belt to select the matching item for secondary screening.

In an embodiment, the system 200 can be based on a Smiths Detection® X-ray system, having a belt length of approximately 324-330 inches, a full cycle of belt with no alarms of 35.83 seconds (9 seconds per inch), a last item to calibration mode of 7.16 seconds/64.44 inches, and a calibration mode to scan mode of 3.39 seconds/30.51 inches. In such a system, markers can be applied to the belt as follows: 11 total markers, placed using a series of X-ray reactive markers 0, 1, 2, 3, 0, 1, 2, followed by a series of visual markers 0, 1, 2, 3.

More specifically, in such an embodiment the markers can be placed according to the following procedure, which can be customized to suit given dimensions of a belt and upper/lower X-ray offsets, as well as a particular type of orientation/operation (e.g., belt direction, tube location, etc.) of a given type of X-ray system, but is presented here with respect to the Smiths Detection® X-ray system:

1. Clean belt with alcohol and let dry before application of numbers. BOLD numbers indicate X-ray reactive markers, and underlined numbers indicate visual markers.
2. Set the reflective "0"
3. Set next reflective number "1" 35.25 inches from "0"
4. Set next reflective number "2" 30 inches from "1"
5. Set next reflective number "3" 30 inches from "2"
6. Use vinyl tape to set following reflective numbers as they may have to be adjusted to properly "ghost" numbers in steps 2 thru 5
7. Use vinyl tape to temporarily set reflective number "0" 27.25 inches from "3"
8. Use vinyl tape to temporarily set reflective number "1" 35.25 inches from "0"
9. Use vinyl tape to temporarily set reflective number "2" 30 inches from "1"
10. Run the belt and double check using bowls that reflective numbers in steps 7-9 are in proper place. Make adjustments as necessary and then remove vinyl tape to set numbers placed in steps 7-9
11. Set mailbox number "0" (approx. 21⅛ from X-ray reactive "2")
12. Use bowls as markers and make sure "0" set in step 11 is in the right place. Adjust accordingly.
13. Set mailbox number "1" 35.25 inches from "0"
14. Set mailbox number "2" 30 inches from "1"

15. Set mailbox number "3" 30 inches from "2"
16. Load belt and make sure that numbers are marking correctly. This is also easy to check if you start using lane as live lane because there are lots of points of reference as passengers place their items to fully load belt.
   Note: Numbers may need adjustment based on where the tube head is located (next to vs. opposite side of x-ray operator) and direction of belt. Measurements discussed above are only for Smiths X-ray machines.

Overview: START set reflective "0"—35.25 inches—set "1"—30 inches—set "2"—30 inches—set "3"—27.25 inches—set "0"—35.25 inches—set "1"—30 inches—set "2"—approx. 21⅛ inches—set "0"—35.25 inches—set "1"—30 inches—set "2"—30 inches—set "3" END.

To measure between markers, a common reference point can be used. For example, the markers can be contained within consistently sized rectangles, and measurements can be taken from a consistent location on each marker. For example, a midpoint of the horizontal edge of a marker can be used to take a measurement, such that distances between markers are based on distances between the midpoints of markers. Alternatively, other points can be used, such as using the top left corner of each marker to take measurements between markers, such that using the same consistent point on each marker produces proper and consistent alignment for the entire belt.

In another embodiment, the system 200 can be based on a Rapiscan® Systems X-ray system, having a belt length of approximately 249.5 to 254 inches, a full cycle of belt no alarms of 29.23, 29.96, –30 seconds, and which does not use a last item to calibration mode or a calibration mode to scan mode. In such a system, markers can be applied to the belt for a "left" configured system as follows: 22 total markers, placed using a series of X-ray reactive markers 0, 1, 2, 3, 4, 5, 0, 1, 2, 3, 0, 1, followed by a series of visual markers 2, 3, 4, 5, 0, 1, 2, 3, 0, 1. For a "right" configured system, the markers can be placed as follows: 22 total markers, placed using a series of X-ray reactive markers 0, 1, 2, 3, 4, 5, 0, 1, 2, 3, 0, 1, followed by a series of visual markers 0, 1, 2, 3, 4, 5, 0, 1, 2, 3. A similar placement procedure can be used to place the markers on the belt, adjusted for distance accordingly to complete a circuit around the entire belt.

Because such a system does not involve a calibration approach associated with a minimum span of belt without X-ray reactive markers, a relatively larger number of markers (e.g., 22 total markers) can be used, compared to other systems that may use fewer numbers in order to leave additional space between X-ray reactive markers. Furthermore, use of a pattern of visual markers enables a portion of the belt to remain free of X-ray reactive markers over a number of instances of marker placement, which provides sufficient room for an auto-calibration function of the X-ray system, if applicable.

Figure 3:
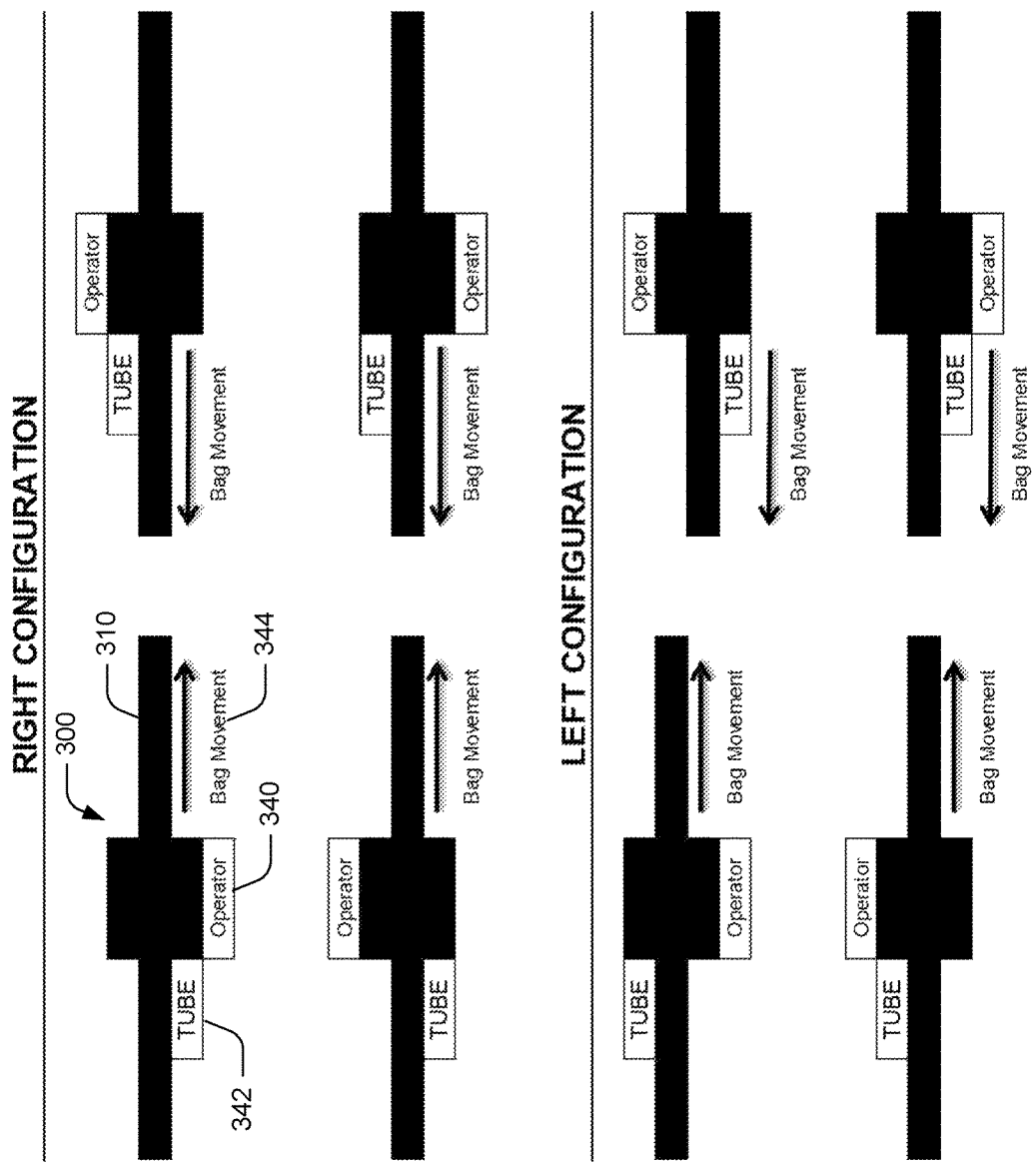
FIG. 3 illustrates example systems including different configurations of tube, operator, and bag movement.

FIG. 3 illustrates example systems 300 including different configurations of tube 342, operator 340, and bag movement 344. The tube allows the operator to pull a scanned item from the main belt and transfer the item to an MDR for further inspection. As illustrated, a given machine can involve different "right" configurations and "left" configurations. Such different combinations can result in corresponding different spatial synchronizations of the various markers. For example, as described above for the Rapiscan® Systems X-ray system, a specifically different pattern of markers can be used for the "left" vs "right" configurations.

Figure 4:
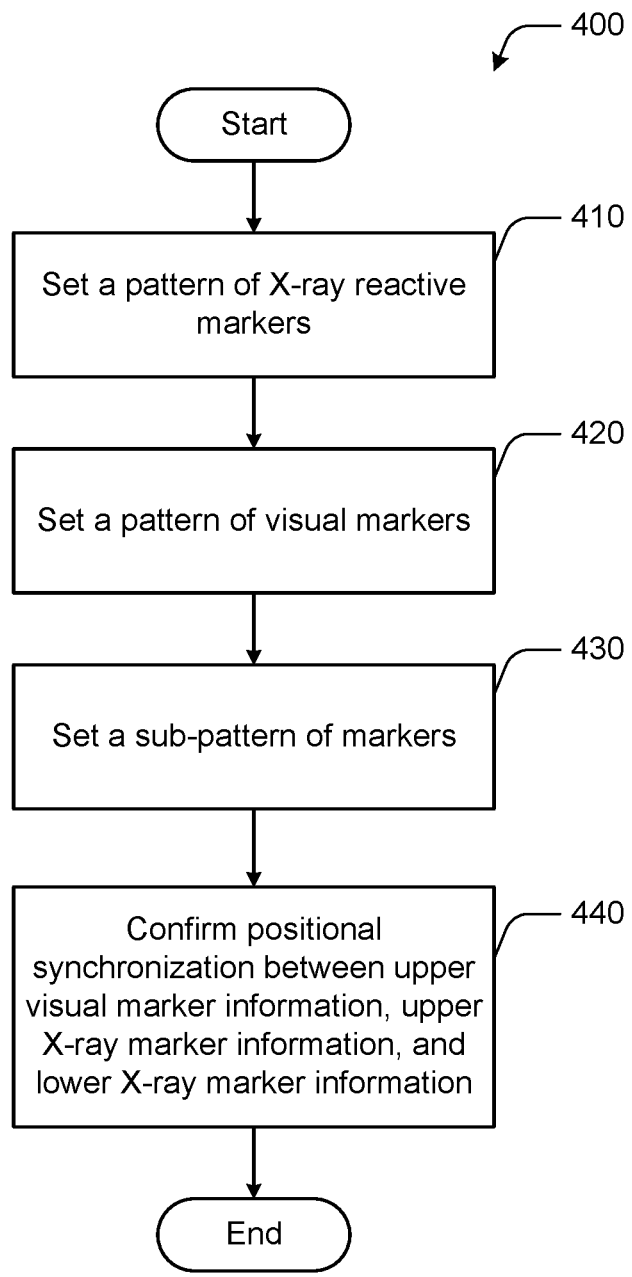
FIG. 4 is a flowchart illustrating a method of setting synchronized markers on a belt.

FIG. 4 is a flowchart 400 illustrating a method of setting synchronized markers on a belt. A pattern of X-ray reactive markers are set on the belt (410). For example, the X-ray reactive markers can be spaced apart along the belt, to accommodate items to be placed on the belt between markers for conveying through an X-ray system. In an embodiment, the pattern of spaced apart X-ray reactive markers occupies less than half of the circumference of the belt, as illustrated for example by the pattern 224A of FIG. 2 including markers 3, 2, 1, 0. The markers can include other symbols, such as visually distinct groupings of items like dots or rods. For example, instead of a marker "1," a single rod or thread can be included within the belt. Such a rod or thread could extend at least partially across a width of the belt to be visible from a top view X-ray. The thread/rod-based marker is also visible from a side view X-ray, whereby the rod would appear as a dot within the belt. Similarly, the marker "4" could be represented by a grouping of four threads/rods, which would be visible from the top or side X-rays.

The X-ray reactive markers can be placed on an outer surface, an inner surface, or within the belt. In some embodiments, the X-ray reactive marker can serve as its own visual marker, by being placed on an outer surface of the belt. In other embodiments, the X-ray reactive marker can be protected within the belt or on an inner surface of the belt, and a corresponding visual marker can be used to mark the same belt location on the outer surface of the belt corresponding to the X-ray reactive marker.

A pattern of visual markers are set on the belt (420). A similar approach described above with respect to the pattern of X-ray reactive markers can be used for the visual markers. However, because the visual markers serve to be visible by operators, the visual markers are placed on an outer surface of the belt. Accordingly, when revolved such that the visual marker is positioned on an underside of the belt, the visual marker will not be visible. Accordingly, embodiments take advantage of such properties to be able to synchronize marker placements such that an arrangement can involve a visual marker placement before one X-ray scanner that does not match a corresponding marker that is positioned before the other X-ray scanner. For example, consider how the visual marker 0 depicted on a belt underside in FIG. 2 does not numerically match with the X-ray reactive marker 3 on the upper side of the belt. However, no inconsistency is encountered, because the composite X-ray results in the same marker information as the visual marker information seen by an operator looking at the belt.

The patterns used for the X-ray reactive markers and visual markers shown in FIG. 2 happens to be the same four symbols/numbers 0, 1, 2, 3, 4. However, in some embodiments, different patterns are used (consider, e.g., the above-described example of the "left" configured Rapiscan® Systems X-ray system, in which the pattern of marker types differs. Furthermore, the difference between patterns can include differences in total length of markers as well as the sequence of markers.

A sub-pattern of markers are set on the belt. The sub-pattern can be based on the pattern of X-ray reactive markers, and/or based on the visual markers. In the example of FIG. 2, the sub-pattern is based on both of the patterns, because the patterns are equal to each other. The sub-pattern can be formed from X-ray reactive markers, visual markers or a combination of both.

The positional synchronization between upper visual marker information, upper X-ray marker information, and lower X-ray marker information is confirmed (440). Such confirmation can be performed by, e.g., installing the belt on a machine and ensuring that belt stretch does not cause the markers to become misaligned. If a given belt system has predictable belt stretch upon belt installation and machine operation, then such information can be used when determining the various distances between marker positions. In other embodiments, such as those where markers are placed on an existing belt, the X-ray system can be operated to check positioning visually and/or by X-ray, and whether the overlapping markers are aligned. Individual markers can be placed using temporary adhesive such as tape, and after confirming positional synchronization, the markers can be placed using more permanent adhesive such as glue or cement. Additional types of confirmations can include verifying that the predetermined type of marker spacing corresponds to the particular X-ray system type and belt direction. For example, eight different types of configurations are illustrated in FIG. 3 for a given machine. Accordingly, it is possible that a given "correct" marker positioning for a belt could end up being "incorrect" if the belt is used on an incompatible configuration or belt direction.

FIGS. 5A-5F illustrate an operation of an example system including synchronized markers 520 apparent in a composite X-ray 531. Visual markers 524 are indicated as white numbers on a black background. X-ray reactive markers 522 are indicated as black numbers without a background. The upper and lower X-ray scanners are omitted for clarity, but the misalignment between the corresponding upper and lower X-rays is represented by a diagonal arrow labeled as the X-ray offset 508. In FIG. 5A, the X-ray offset 508 represents an alignment between the lower visual marker "0" and the upper X-ray reactive marker "3." Similarly, the lower X-ray reactive marker "2" is aligned with the upper X-ray reactive marker "2." Such information is visible on the top down composite X-ray view 531. The side composite X-ray view 538 does not show the numbers, but in alternate embodiments, a thicker marker such as rods can be used within the belt to be visible from both the top and side X-rays. Rotation of the belt 510 is indicated with curved directional arrows. The top down visual appearance 520 illustrates what is visible on an upper outer surface of the belt 510. Markers are visible within the upper scanned belt section 535, as well as the tube 542. If an item is flagged to be pulled, then it will be pulled from the tube section 542.

Figure 5B:
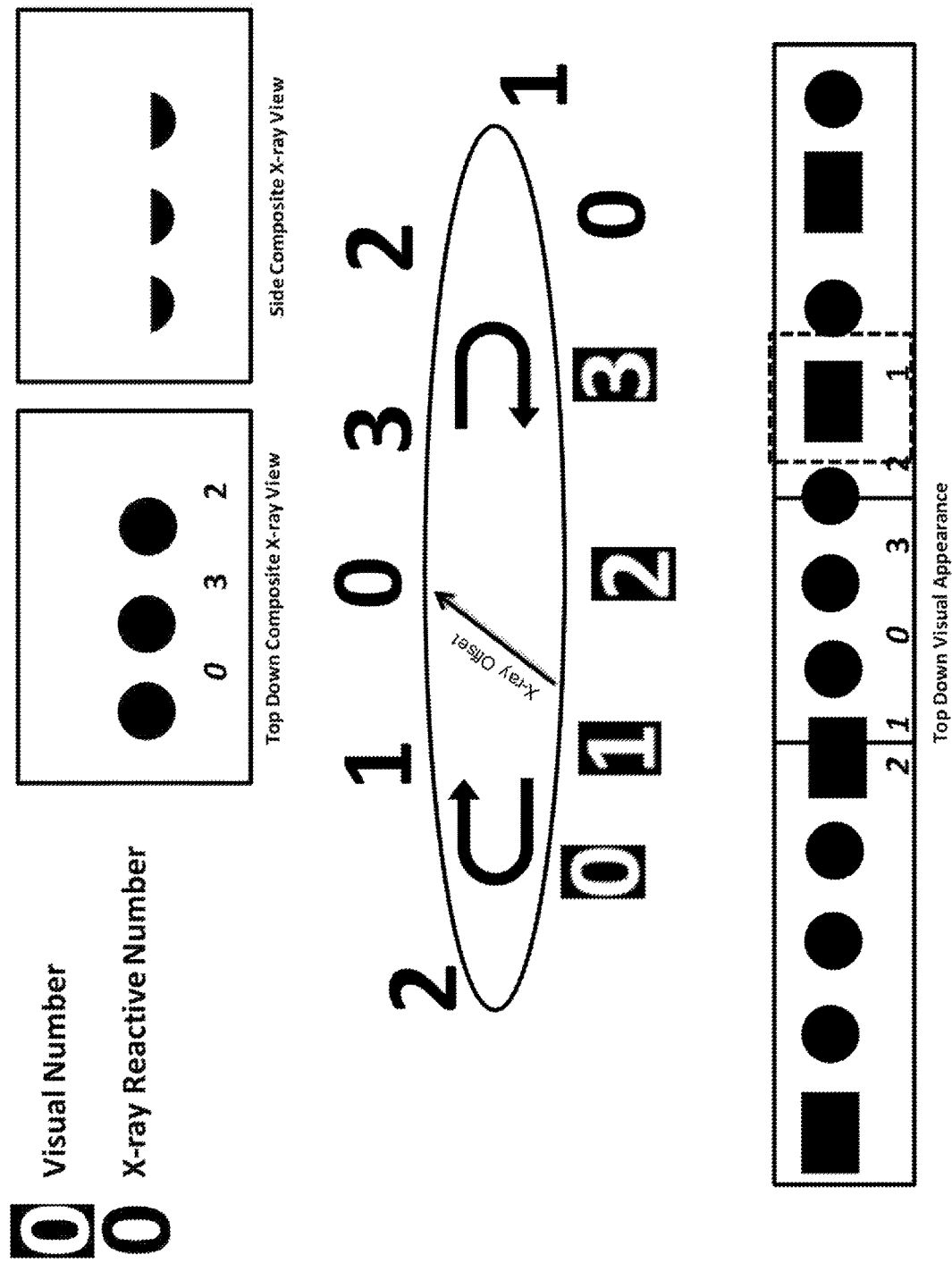
Figure 5C:
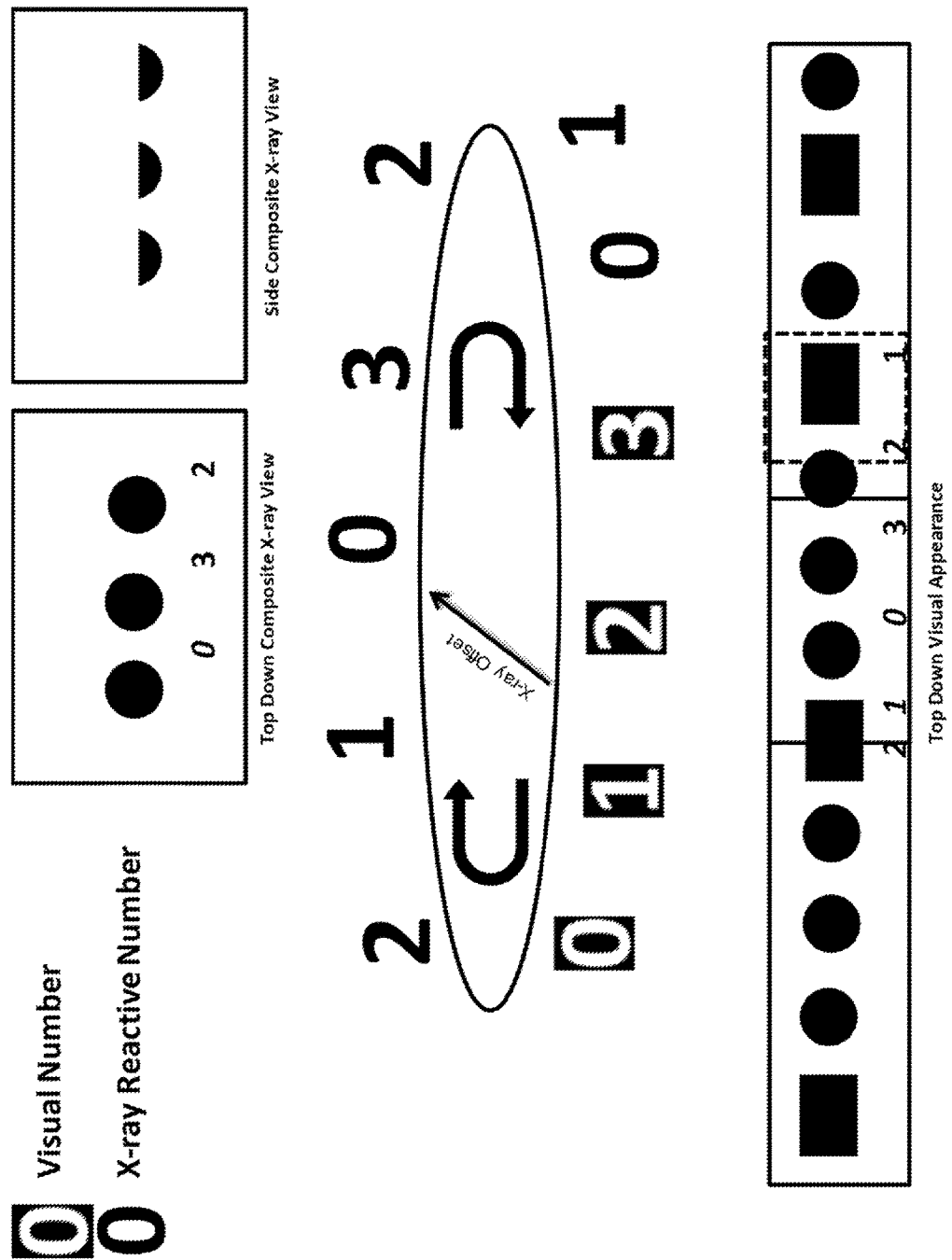
Figure 5D:
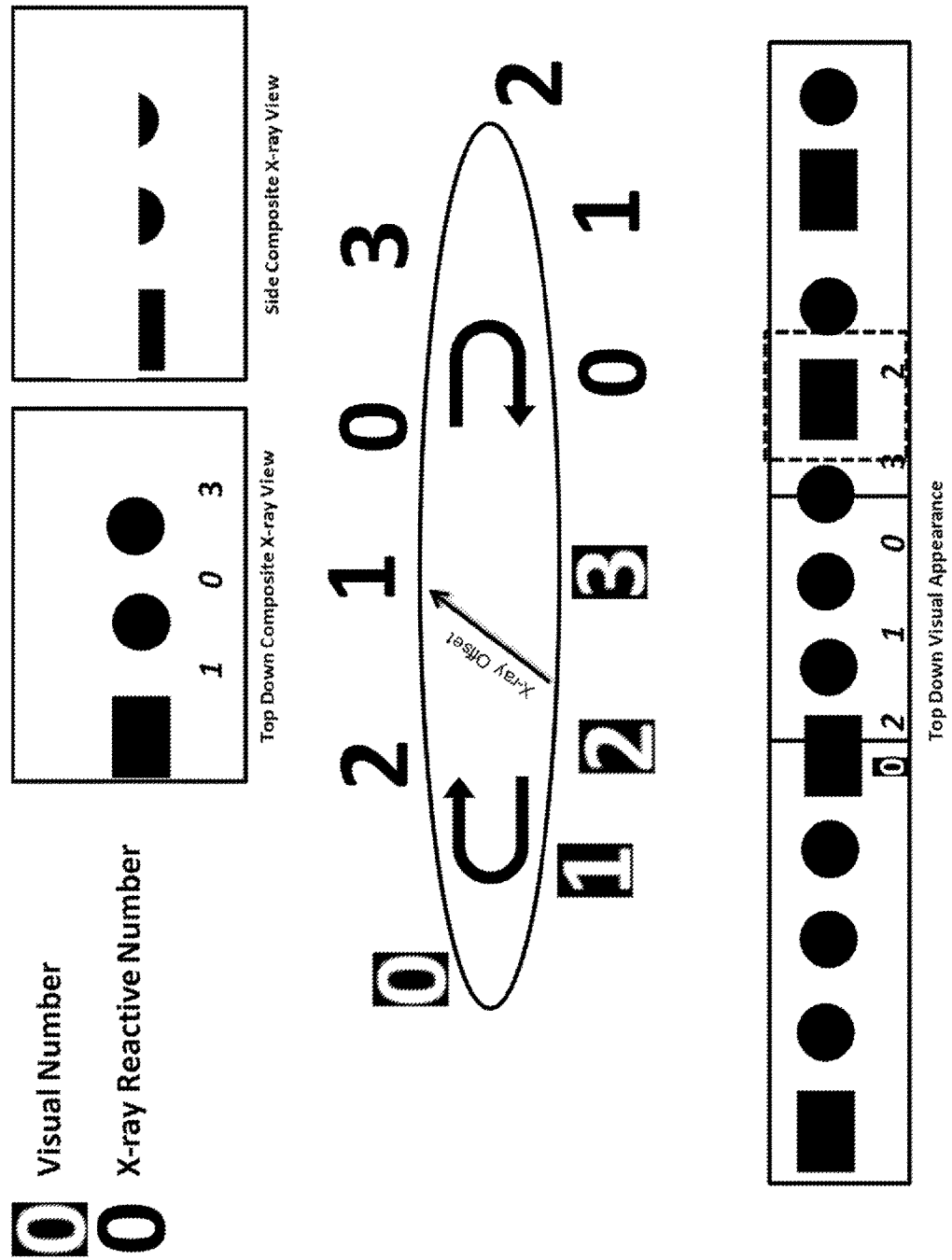
Figure 5E:
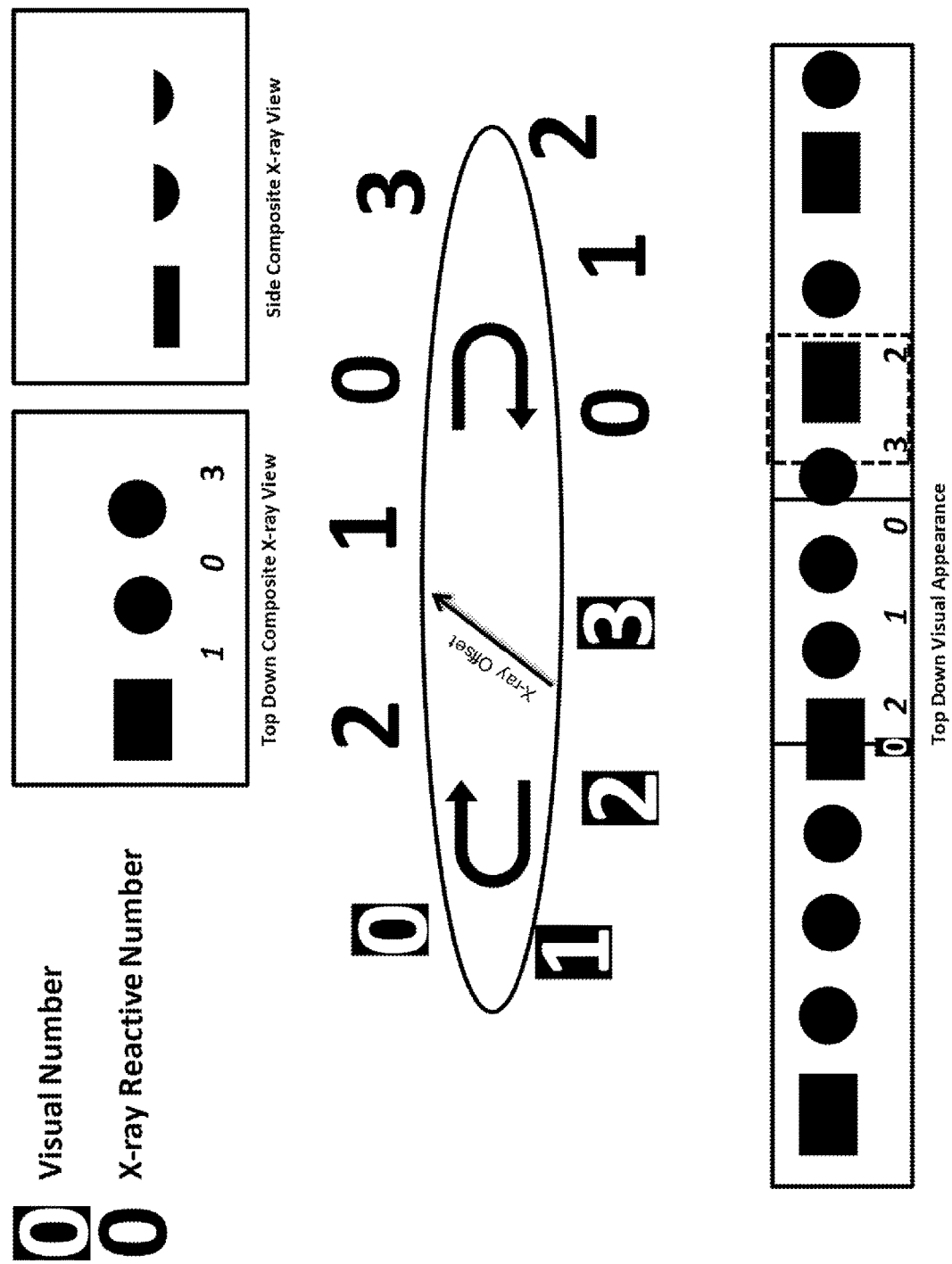
Figure 5F:
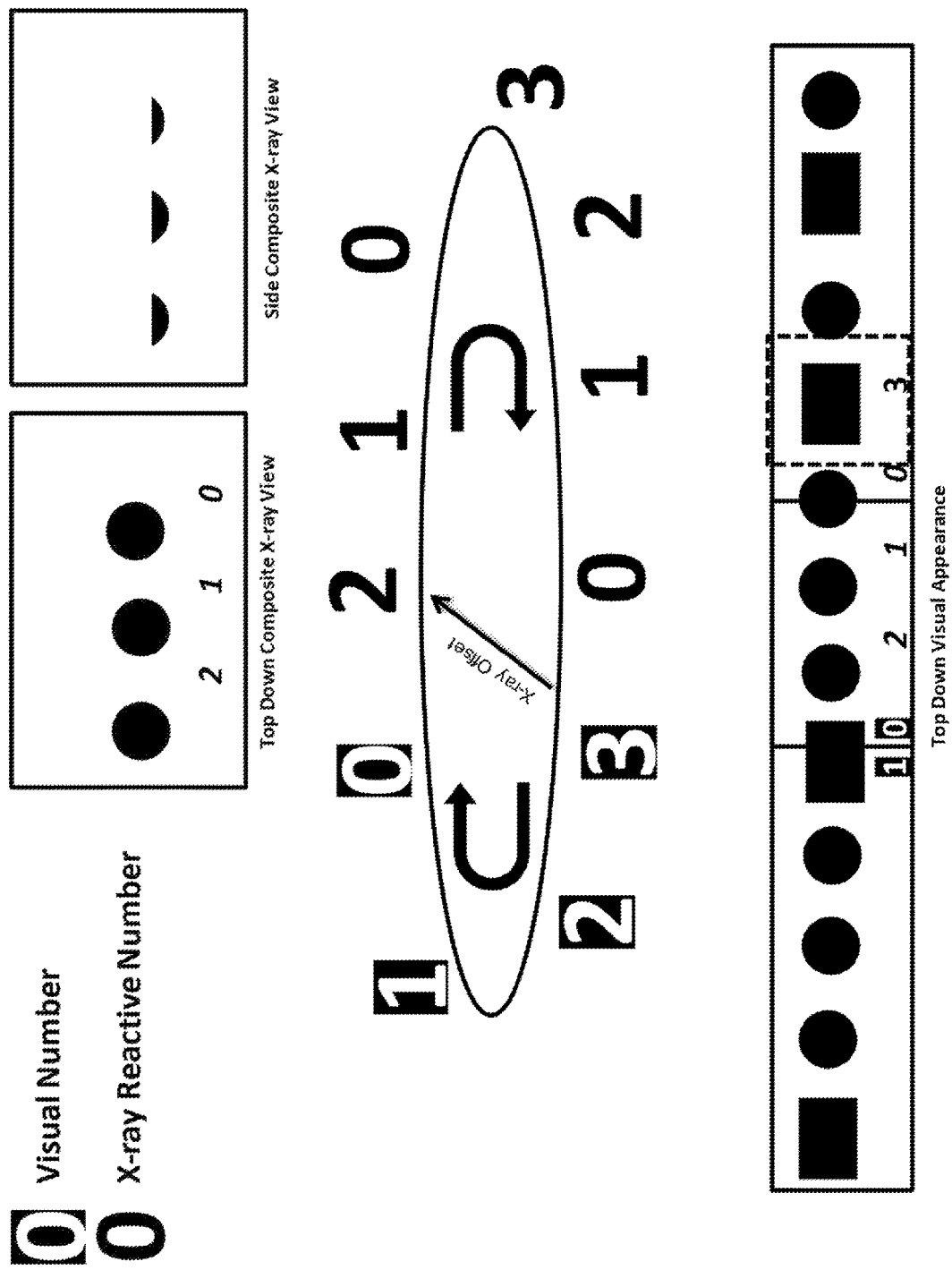

Successive FIGS. 5B-5F illustrate the same elements, but with progressively advancing belt positions. For example, FIG. 5B illustrates the belt 510 advanced such that the upper X-ray reactive marker "0" is aligned with the lower visual marker "1." However, as shown in the top down composite X-ray view, the "0" marker is seen in the X-ray consistent with the top down visual appearance. Also apparent is that the X-ray does not perfectly align with the visual appearance, because of various delays or offsets between not only the plurality of X-ray scanners, but also between either of the scanners and the physical belt movement itself. For example, the X-ray can maintain an image of an item and marker, such as marker 2 in FIG. 5B top down composite X-ray view, even though the top down visual appearance shows that the marker 2 has already exited the X-ray scanner area and is now located in the tube. FIG. 5C shows the marker "2" has further advanced into the tube of the top down visual appearance of the belt. FIG. 5D shows further advancement where the upper X-ray reactive marker "1" is aligned with the lower visual marker "2." FIG. 5E shows further belt advancement, with the markers "3" and "2" further advanced through the tube. FIG. 5F shows the belt further advanced with the upper X-ray sensitive marker "2" aligned with the lower visual marker "3." Such belt movement can continue indefinitely, while constantly displaying consistent composite X-ray marker information, which also matches consistently with the visual information that is apparent by an operator viewing the top belt surface.

Note that, due to the nature of the multiple-scanner X-ray systems, the upper and lower X-rays show consistent movement of markers in the same direction. While the physical motion of the markers on the belt appear to cross each other in opposite directions, from the viewpoint of the upper and lower X-ray scanners, the markers appear to travel in the same direction. Accordingly, the composite X-ray image depicts the synchronized number smoothly moving across the screen, without ever providing inconsistent information. Even in situations of misalignment, the markers are still clearly understandable and distinct, regardless of belt position.

As illustrated and described above, the placement of the reference markers enables the composite X-ray images to be consistent with a visual appearance, based on the combined use of visual markers (which do not appear on either X-ray image, but which are evident in the visual appearance of the belt) and X-ray reactive markers (which appear in either X-ray image, and which can be evident in the visual appearance of the belt if placed on an outer surface of the belt, and if placed visually concealed on an inner surface of the belt, a corresponding visual marker can be placed on the outer surface corresponding to the location of the hidden X-ray reactive marker).

Due to the synchronized placement of numbers, at no point will a conflict arise in the marker information appearing in either X-ray or forming the visual appearance of the belt. More specifically, the visual appearance of the belt will not be inconsistent with the X-ray images, including the upper X-ray image, the lower X-ray image, and the composite X-ray image.

While a number of example embodiments of the present invention have been described, it should be appreciated that the present invention provides many applicable inventive concepts that can be embodied in a wide variety of ways. The example embodiments discussed herein are merely illustrative of ways to make and use the invention and are not intended to limit the scope of the invention. Rather, as will be appreciated by one of skill in the art, the teachings and disclosures herein can be combined or rearranged with other portions of this disclosure and the knowledge of one of ordinary skill in the art.

Terms and phrases used in this document, unless otherwise expressly stated, should be construed as open ended as opposed to closed—e.g., the term "including" should be read as meaning "including, without limitation" or the like; the term "example" is used to provide example instances of the item in discussion, not an exhaustive or limiting list thereof; the terms "a" or should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Furthermore, the presence of broadening words and phrases such as "one or more," "at least," "but not limited to," or other similar phrases, should not be read to mean that the narrower case is intended or required in instances where such broadening phrases may be absent. Any headers used are for convenience and should not be taken as limiting or restricting. Additionally, where this document refers to technologies that would be apparent or known to one of ordinary skill in the art, such technologies encompass those apparent or known to the skilled artisan now or at any time in the future.

What is claimed is:

1. A multiple-scanner X-ray system including synchronized reference markers, comprising:
    a belt to convey items through the X-ray system, wherein an upper belt portion is conveyed in a first direction above a sliding bed of the X-ray system, and a lower belt portion is conveyed in a second direction opposite the first direction below the sliding bed;
    an upper X-ray scanner to obtain an upper X-ray of an upper scanned belt section above the sliding bed;
    a lower X-ray scanner to obtain, during operation of the upper X-ray scanner, a lower X-ray of a lower scanned belt section below the sliding bed; and
    a plurality of X-ray reactive markers positionally synchronized relative to each other and the belt and conveyed by the belt to cause upper visual marker information, corresponding to a visual appearance of the upper scanned belt section, to be consistent with i) upper X-ray marker information of the upper X-ray, and ii) lower X-ray marker information of the lower X-ray.

2. The multiple-scanner X-ray system of claim 1, wherein the upper X-ray includes an upper offset delay relative to the upper visual marker information, wherein the lower X-ray includes a lower offset delay relative to the lower visual marker information, and wherein the upper X-ray and the lower X-ray portray the belt moving in the same direction.

3. The multiple-scanner X-ray system of claim 1, wherein the upper offset delay is different than the lower offset delay.

4. The multiple-scanner X-ray system of claim 1, further comprising a plurality of visual markers disposed on the belt along with the X-ray reactive markers and arranged to be visually consistent with the upper X-ray and the lower X-ray to avoid a mismatch between the upper visual marker information and the upper X-ray and the lower X-ray.

5. The multiple-scanner X-ray system of claim 4, wherein at least one of the plurality of visual markers is disposed on the belt such that a visual mismatch between the upper X-ray marker information and lower visual marker information, as viewed from the perspective of the lower X-ray, is not apparent due to the lower visual marker information being visually obscured on an underside of the belt and due to X-ray transparency of the visual markers not being displayable in the lower X-ray.

6. The multiple-scanner X-ray system of claim 4, wherein the plurality of visual markers are disposed on outer surface of the belt.

7. The multiple-scanner X-ray system of claim 1, wherein the X-ray reactive markers comprise symbols including numbers.

8. The multiple-scanner X-ray system of claim 1, wherein the X-ray reactive markers are disposed on an inner surface of the belt facing the sliding bed.

9. The multiple-scanner X-ray system of claim 8, wherein a visual marker, matching a respective X-ray reactive marker disposed on the inner surface of the belt, is disposed on an outer surface of the belt to cause the upper visual marker information to match the upper X-ray marker information.

10. The multiple-scanner X-ray system of claim 1, wherein the X-ray reactive markers are embedded at least partially within the belt.

11. The multiple-scanner X-ray system of claim 1, wherein a given X-ray reactive marker comprises a grouping of symbols apparent in a top view X-ray and a side view X-ray.

12. The multiple-scanner X-ray system of claim 1, wherein the plurality of X-ray reactive markers are spaced on the belt to accommodate dimensions of a carry-on baggage item placed between adjacent X-ray reactive markers.

13. The multiple-scanner X-ray system of claim 1, wherein the plurality of X-ray reactive markers are interspersed with a plurality of visual markers transparent to X-rays to allow sufficient length of belt to be conveyed without encountering an X-ray reactive marker, to accomplish operational calibration of the X-ray system.

14. The multiple-scanner X-ray system of claim 1, wherein a circumference of the belt includes an instance of a pattern of X-ray reactive markers and an instance of the same pattern of visual markers, and at least one instance of a sub-pattern, which is a subset section of the pattern, the sub-pattern including X-ray reactive or visual markers.

15. The multiple-scanner X-ray system of claim 1, wherein the system displays a composite X-ray comprising the upper X-ray superimposed on the lower X-ray, and wherein the composite X-ray is consistent with the visual appearance of the upper scanned belt section.

16. The multiple-scanner X-ray system of claim 15, wherein movement of the belt includes coincidences of upper visual marker information and lower X-ray marker information such that the lower X-ray marker information is apparent in the composite X-ray where the upper X-ray marker information is missing, and such that duplicated upper X-ray marker information and lower X-ray marker information is apparent in the composite X-ray as a double X-ray marker.

17. A belt including synchronized reference markers for use in a multiple-scanner X-ray system, comprising:
    a plurality of X-ray reactive markers arranged to be evident in an upper X-ray of an upper scanned belt section above a sliding bed, and in a lower X-ray of a lower scanned belt section below the sliding bed, during belt movement; and
    a plurality of visual markers arranged to be visible as part of upper visual marker information during belt movement;
    wherein the plurality of X-ray reactive markers and the plurality of visual markers are positionally synchronized relative to each other and the belt to cause upper visual marker information, corresponding to a visual appearance of the upper scanned belt section, to be consistent with i) upper X-ray marker information in the upper X-ray, and ii) lower X-ray marker information in the lower X-ray.

18. The belt of claim 17, wherein a given X-ray reactive marker comprises a visually distinct grouping of symbols, wherein the distinct combination of symbols is apparent in an upper top view X-ray and an upper side view X-ray for the upper X-ray marker information, and apparent in a lower top view X-ray and a lower side view X-ray for the lower X-ray marker information.

19. A method of including synchronized reference markers on a belt for use in a multiple-scanner X-ray system, comprising:
    setting on the belt at least one instance of a pattern of a plurality of X-ray reactive markers, the X-ray reactive markers being spaced apart from one another to accommodate items to be scanned;

setting on the belt at least one instance of the pattern of a plurality of visual markers, spaced apart to accommodate items to be scanned;

setting on the belt at least one instance of a sub-pattern comprising X-ray reactive or visual markers, which is a subset section of the pattern, the sub-pattern being formed by markers spaced apart from one another to accommodate items to be scanned;

wherein X-ray reactive markers and the visual markers are spaced from each other and aligned relative to conveyance of an upper belt portion and a lower belt portion of the belt to be positionally synchronized when the belt is used in a multiple-scanner X-ray system to cause upper visual marker information, corresponding to a visual appearance of an upper scanned belt section, to be consistent with i) upper X-ray marker information in an upper X-ray, and ii) lower X-ray marker information in a lower X-ray.

20. The method of claim 19, further comprising setting the X-ray reactive markers on an inside surface of the belt, and setting the visual markers on an outside surface of the belt.

* * * * *